United States Patent
Ward et al.

(10) Patent No.: US 11,744,977 B2
(45) Date of Patent: Sep. 5, 2023

(54) PRODUCT MANIFOLDS FOR USE WITH PORTABLE OXYGEN CONCENTRATORS AND PORTABLE OXYGEN CONCENTRATORS INCLUDING SUCH PRODUCT MANIFOLDS

(71) Applicant: Aventics Corporation, Lexington, KY (US)

(72) Inventors: James R. Ward, Lexington, KY (US); Peizhen Li, Lexington, KY (US)

(73) Assignee: Aventics Corporation, Lexington, KY (US)

(*) Notice: Subject to any disclaimer, the term of this patent is extended or adjusted under 35 U.S.C. 154(b) by 589 days.

(21) Appl. No.: 16/890,649

(22) Filed: Jun. 2, 2020

(65) Prior Publication Data

US 2020/0384233 A1 Dec. 10, 2020

Related U.S. Application Data

(60) Provisional application No. 62/857,665, filed on Jun. 5, 2019.

(51) Int. Cl.
*A61M 16/10* (2006.01)
*A61M 16/00* (2006.01)
(Continued)

(52) U.S. Cl.
CPC ...... *A61M 16/101* (2014.02); *A61M 16/0063* (2014.02); *A61M 16/0093* (2014.02);
(Continued)

(58) Field of Classification Search
CPC ............ A61M 16/101; A61M 16/0063; A61M 16/0093; A61M 16/20; A61M 2202/0208;
(Continued)

(56) References Cited

U.S. PATENT DOCUMENTS

| 4,385,639 | A | 5/1983 | Holborow | |
| 7,763,103 | B2* | 7/2010 | Dolensky | B01D 53/0415 96/130 |
| 7,980,269 | B2 | 7/2011 | Fry et al. | |
| 2006/0117957 | A1* | 6/2006 | McCombs | B01D 53/047 96/121 |
| 2006/0237017 | A1* | 10/2006 | Davidson | A61M 16/0622 128/205.25 |

(Continued)

OTHER PUBLICATIONS

International Search Report and Written Opinion for PCT/US2020/035563, dated Aug. 28, 2020.

*Primary Examiner* — Kathryn E Ditmer
(74) *Attorney, Agent, or Firm* — MARSHALL, GERSTEIN & BORUN LLP

(57) ABSTRACT

Product manifolds for use with portable oxygen concentrators and portable oxygen concentrators including such product manifolds. An example product manifold for use with a portable oxygen concentrator includes a body, a first product port, a second product port, an accumulator port, an output port, and a flow path. The flow path fluidly couples the first product port, the second product port, the accumulator port, and the output port. The product manifold includes a first control port, a second control port, and a third control port. The first, second, and third control ports fluidly couple the flow path. The product manifold also includes a first solenoid valve assembly, a second solenoid valve assembly, and a third solenoid valve assembly. The first, second, and third solenoid valve assemblies are secured to the body of the product manifold adjacent the first, second, and third control ports, respectively, by a corresponding snap fit connector.

13 Claims, 5 Drawing Sheets

(51) Int. Cl.
*A61M 16/20* (2006.01)
*B01D 53/053* (2006.01)
*B01D 53/047* (2006.01)

(52) U.S. Cl.
CPC ........... *A61M 16/20* (2013.01); *B01D 53/047* (2013.01); *B01D 53/053* (2013.01); *A61M 2202/0208* (2013.01); *A61M 2202/0266* (2013.01)

(58) Field of Classification Search
CPC ...... A61M 2202/0266; A61M 16/0816; B65D 41/16; B65D 45/04; B65D 45/18; B65D 45/22; B65D 41/46; B01D 53/04; B01D 53/0415; B01D 53/047; B01D 53/053
See application file for complete search history.

(56) References Cited

U.S. PATENT DOCUMENTS

| | | | |
|---|---|---|---|
| 2009/0065007 A1* | 3/2009 | Wilkinson | A61M 16/0069 96/108 |
| 2010/0252760 A1 | 10/2010 | Hettinger | |
| 2010/0301245 A1 | 12/2010 | Accurso et al. | |
| 2012/0192864 A1* | 8/2012 | Galbraith | B01D 53/26 96/111 |
| 2015/0231550 A1 | 8/2015 | Morita | |
| 2015/0260308 A1 | 9/2015 | Fry et al. | |
| 2016/0158477 A1* | 6/2016 | Dhuper | A61M 16/14 128/200.23 |
| 2017/0361052 A1* | 12/2017 | Taylor | A61M 16/101 |
| 2021/0113801 A1* | 4/2021 | Wang | A61M 16/0051 |

* cited by examiner

PRODUCT MANIFOLDS FOR USE WITH PORTABLE OXYGEN CONCENTRATORS AND PORTABLE OXYGEN CONCENTRATORS INCLUDING SUCH PRODUCT MANIFOLDS

FIELD OF THE DISCLOSURE

The present disclosure relates generally to product manifolds and, in particular, to product manifolds for use with portable oxygen concentrators and portable oxygen concentrators including such product manifolds

BACKGROUND

Portable oxygen concentrators may be used as an alternative to portable oxygen tanks. In operation, portable oxygen concentrators compress and purify ambient air allowing for oxygen-rich air to be delivered to a user.

SUMMARY

In accordance with a first example, a product manifold for use with a portable oxygen concentrator includes a body, a first product port, a second product port, an accumulator port, an output port, and a flow path. The flow path fluidly couples the first product port, the second product port, the accumulator port, and the output port. The product manifold includes a first control port, a second control port, and a third control port. The first, second, and third control ports fluidly couple the flow path. The product manifold also includes a first solenoid valve assembly, a second solenoid valve assembly, and a third solenoid valve assembly that are secured to the body of the product manifold adjacent the first, second, and third control ports, respectively, by a corresponding snap fit connector.

In accordance with a second example, a portable oxygen concentrator includes a compressor and a waste/feed manifold. The waste/feed manifold includes an inlet port coupled to the compressor and a pair of three-way valves. Each three-way valve has a first port, a second port, and a third port. The first port is coupled to the compressor. The waste/feed manifold includes an exhaust port. The second port of each of the three-way valves is fluidly coupled to the exhaust port. The portable oxygen concentrator includes a first sieve bed and a second sieve bed. Each of the sieve beds is coupled to the third port of one of the three-way valves. The portable oxygen concentrator includes a product manifold including a body and a first product port and a second product port. The first product port is coupled to the first sieve bed and the second product port is coupled to the second sieve bed. The product manifold also includes an accumulator port, an output port, and a flow path. The flow path fluidly couples the first product port, the second product port, the accumulator port, and the output port. The product manifold includes a first control port, a second control port, and a third control port. The first, second, and third control ports fluidly couples the flow path. The portable oxygen concentrator includes a first solenoid valve assembly, a second solenoid valve assembly, and a third solenoid valve assembly that are secured to the body of the product manifold by a corresponding snap fit connector.

In accordance with a third example, a product manifold for use with a portable oxygen concentrator includes a body, a first product port, a second product port, an accumulator port, an output port, and a flow path. The flow path fluidly couples the first product port, the second product port, the accumulator port, and the output port. The product manifold includes a control port that fluidly couples the flow path. The product manifold includes a solenoid valve assembly that is secured to the body of the product manifold by a snap fit connector. The snap fit connector includes a first ramp, a second ramp, a first opening, and a second opening. The first opening is adapted to receive the first ramp and the second opening is adapted to receive the second ramp to form the snap fit connector between the solenoid valve assembly and the body of the product manifold.

In further accordance with the foregoing first, second, and/or third examples, an apparatus may further include any one or more of the following:

In accordance with one example, the first solenoid valve assembly includes a first opening and a second opening and the body of the product manifold includes a first ramp and a second ramp. The first ramp being disposed on a first side of the first control port and the second ramp is disposed on a second side of the first control port. The first opening is adapted to receive the first ramp and the second opening is adapted to receive the second ramp to form the snap fit connector between the first solenoid valve assembly and the body of the product manifold.

In accordance with another example, the first ramp is a T-shaped ramp and the first opening is a T-shaped opening.

In accordance with another example, the first solenoid valve assembly includes a first solenoid valve and a first bracket. The first bracket includes the first opening and the second opening.

In accordance with another example, the first solenoid valve includes a housing that has a groove. A portion of the first bracket is disposed within the groove.

In accordance with another example, the first bracket is a U-shaped bracket. The first solenoid valve has a first side, a second side, and a third side. The portion of the U-shaped bracket is received within the groove and surrounds a portion of the first side, the second side, and the third side of the first solenoid valve.

In accordance with another example, the U-shaped bracket includes a first leg and a second leg. The first leg defines the first opening and engages the first side of the first solenoid valve. The second leg defines the second opening and engages the second side of the first solenoid valve.

In accordance with another example, each of the first, second, and third solenoid valve assemblies is secured to the body of the product manifold adjacent to a corresponding one of the first, second, or third control ports by a corresponding snap fit connector.

In accordance with another example, the first solenoid valve assembly includes a first housing having an opening facing the first control port, a control element disposed within the first housing and shiftable between a first position and a second position relative to the first control port.

In accordance with another example, further including a control element guide having a bore and being disposed in the first housing. The control element is at least partially disposed within the bore of the control element guide.

In accordance with another example, the control element guide includes a first portion and a second portion. The first portion is disposed adjacent the opening. Further including a biasing element that is disposed between the first portion of the control element guide and the body of the product manifold to bias the snap fit connector between the first solenoid valve assembly and the body of the product manifold."

In accordance with another example, the first portion of the control element guide forms a spring seat. The biasing element engages the spring seat.

In accordance with another example, further including a plug. The biasing element is disposed between the plug and the first portion of the control element guide.

In accordance with another example, the plug includes a collar and the first control port includes an inner surface. The collar includes a seal groove. Further including a seal that is disposed within the seal groove and is adapted to sealingly engage the inner surface of the first control port.

In accordance with another example, the body of the product manifold includes a first side, a second side, and a third side.

In accordance with another example, the first product port and the second product port extend from the first side of the body and the accumulator port and the output port extend from the second side of the body.

In accordance with another example, the first control port, the second control port, and the third control port are disposed along the third side of the body.

In accordance with another example, the snap fit connectors are formed between the solenoid valve assembly and the body of the product manifold.

In accordance with another example, the first solenoid valve assembly includes a first opening and a second opening and the product manifold includes a first ramp and a second ramp. The first ramp is disposed on a first side of the first control port and the second ramp is disposed on a second side of the first control port. The first opening is adapted to receive the first ramp and the second opening is adapted to receive the second ramp to form the snap fit connector between the first solenoid valve assembly and the body of the product manifold.

In accordance with another example, the first ramp is disposed on a first side of the control port and the second ramp is disposed on a second side of the control port. The first opening is defined by the solenoid valve assembly and the second opening is defined by the solenoid valve assembly.

DETAILED DESCRIPTION

Although the following text discloses a detailed description of example methods, apparatus, and/or articles of manufacture, it should be understood that the legal scope of the property right is defined by the words of the claims set forth at the end of this patent. Accordingly, the following detailed description is to be construed as examples only and does not describe every possible example, as describing every possible example would be impractical, if not impossible. Numerous alternative examples could be implemented, using either current technology or technology developed after the filing date of this patent. It is envisioned that such alternative examples would still fall within the scope of the claims.

Figure 1:
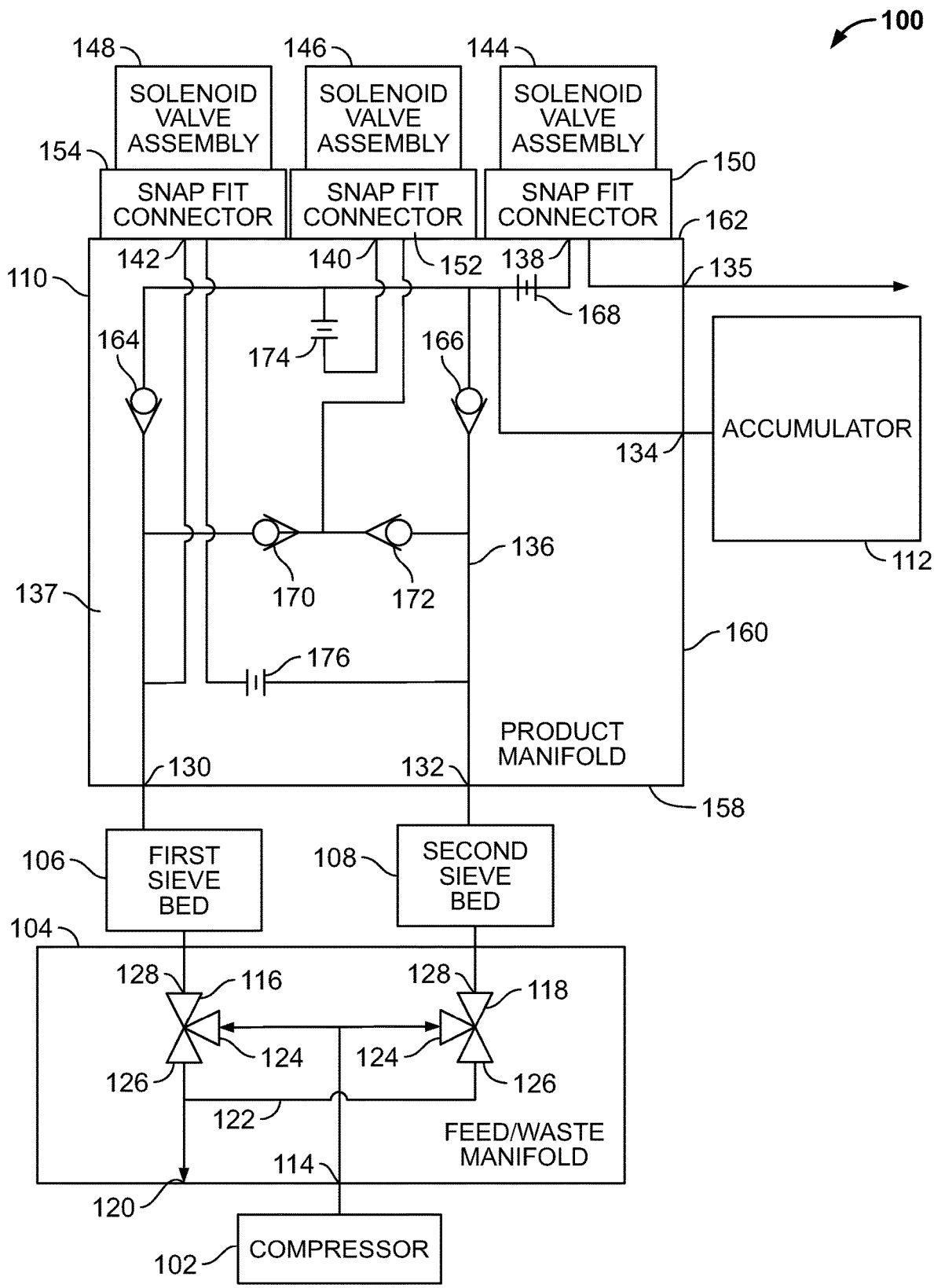
FIG. 1 illustrates a portable oxygen concentrator assembled in accordance with a first disclosed example of the present invention.

Referring now to the drawings, FIG. 1 illustrates a portable oxygen concentrator 100 assembled in accordance with a first disclosed example of the present invention. In accordance with the disclosed example, the portable oxygen concentrator 100 includes a compressor 102, a waste/feed manifold 104, first and second sieve beds 106, 108, a product manifold 110, and an accumulator 112.

The compressor 102 is adapted to draw in ambient air, compress that air, and provide the compressed air to the waste/feed manifold 104.

The waste/feed manifold 104 is adapted to receive the compressed air from the compressor 102 and provide the compressed ambient air to the sieve beds 106, 108. The waste/feed manifold 104 is also adapted to receive nitrogen rich air from the sieve beds 106, 108 during a purge operation.

In the example shown, the waste/feed manifold 104 includes an inlet port 114, a pair of three-way valves 116, 118, an exhaust port 120, and a flow path 122. The inlet port 114 of the waste/feed manifold 104 is coupled to the compressor 102. Each of the valves 116, 118 includes a first port 124, a second port 126, and a third port 128. The first port 124 of each of the valves 116, 118 of the waste/feed manifold 104 is coupled to the compressor 102 via the inlet port 114 and the flow path 122. The second port 126 of each of the valves 116, 118 of the waste/feed manifold 104 is coupled to the exhaust port 120 via the flow path 122.

The first sieve bed 106 and the second sieve bed 108 are each coupled to the third port 128 of one the valves 116, 118. The sieve beds 106, 108 are adapted to adsorb nitrogen from the pressurized ambient air received from the waste/feed manifold 104, for example.

The product manifold 110 is adapted to receive oxygen-rich air from the sieve beds 106, 108 and to provide the oxygen-rich air to the accumulator 112 or to a patient. The product manifold 110 is also adapted to perform a purging operation where a portion of the oxygen-rich air is back flushed through the sieve beds 106, 108 to remove accumulated nitrogen within the sieve beds 106, 108. The nitrogen removed from the sieve beds 106, 108 can thereafter be exhausted via the exhaust port 120 of the feed/waste manifold 104.

In the example shown, the product manifold 110 includes a first product port 130, a second product port 132, an accumulator port 134, an outlet port 135, and a flow path 136. The first product port 130 is coupled to the first sieve bed 106 and the second product port 132 is coupled to the second sieve bed 108. The flow path 136 fluidly couples the first product port 130, the second product port 132, the accumulator port 134, and the output port 135.

The product manifold 110 also includes a body 137, a first control port 138, a second control port 140, and a third control port 142. The first, second, and third control ports 138, 140, 142 fluidly couple portions of the flow path 136. In the example shown, the first control port 138 is an oxygen conserving device (OCD) port, the second control port 140 is a purge port, and the third control port 142 is an equalization port. However, the arrangement of the control ports 138, 140, 142 may be changed. Further, a different number of control ports (e.g., 1 control port, 2 control ports, 4 control ports) may be provided.

The product manifold 110 includes a first solenoid valve assembly 144, a second solenoid valve assembly 146, and a third solenoid valve assembly 148. Each of the first, second, and third solenoid valve assemblies 144, 146, 148 is secured to the body 137 of the product manifold 110 by a snap fit connector 150, 152, 154. Specifically, each solenoid valve assembly 144, 146, 148 is secured to the body 137 of the product manifold 110 adjacent to a corresponding one of the first, second, or third control ports 138, 140, 142 by the corresponding snap fit connector 150, 152, 154. Thus, the solenoid valve assemblies 144, 146, 148 are adapted to control fluid flow through the respective control ports 138, 140, 142.

The snap fit connectors 150, 152, 154 are formed between the solenoid valve assemblies 144, 146, 148 and the body 137 of the product manifold 110. The body 137 has a first side 158, a second side 160, and a third side 162. In the example shown, the first product port 130 and the second product port 132 extend from the first side 158 of the body 137 and the accumulator port 134 and the output port 135 extend from the second side 160 of the body 137. Additionally, in the example shown, the first control port 138, the second control port 140, and the third control port 142 are disposed along the third side 162 of the body 137. However, in other examples, the one or more of the ports 130, 132, 134, 135, 138, 140, 142 may be arranged differently. For example, all of the ports 130, 132, 134, 135, 138, 140, 142 may be positioned on one side of the body 137 of the product manifold 110. Alternatively, one or more of the ports 130, 132, 134, 135, 138, 140, 142 may be positioned on any one of the sides 158, 160, 162 and/or different sides of the body 137.

The product manifold 110 also includes a first check valve 164 and a second check valve 166. The first check valve 164 is associated with receiving air from the first sieve bed 106 and the second check valve 166 is associated with receiving air from the second sieve bed 108. The check valves 164, 166 are adapted to allow the flow of oxygen-rich air from the sieve beds 106, 108 toward the accumulator 112 or the first control port 138. Specifically, to allow the oxygen-rich air received from the sieve beds 106 and/or 108 to flow out of the outlet port 135 of the product manifold 110, the first solenoid valve assembly 144 moves to the open position to allow the oxygen-rich air to flow through an OCD orifice 168, the first control port 138, and out of the outlet port 135 toward, for example, a patient.

The product manifold 110 also includes a third check valve 170 and a fourth check valve 172. The third check valve 170 is associated with flowing air toward the first sieve bed 106 during a purge operation and the fourth check valve 172 is associated with flowing air toward the second sieve bed 108 during a purge operation. Specifically, during a purge operation, the second solenoid valve assembly 146 moves to an open position and allows the oxygen rich air to back flow through a purge orifice 174, through the second control port 140, through the third and fourth check valves 170, 172 and toward the sieve beds 106, 108.

In the example shown, to perform an equalization operation between the first and second sieve beds 106, 108, the third solenoid valve assembly 148 moves to the open position to allow air to flow between the first sieve bed 106 and the second sieve bed 108 and through an equalization orifice 176.

Figure 2:
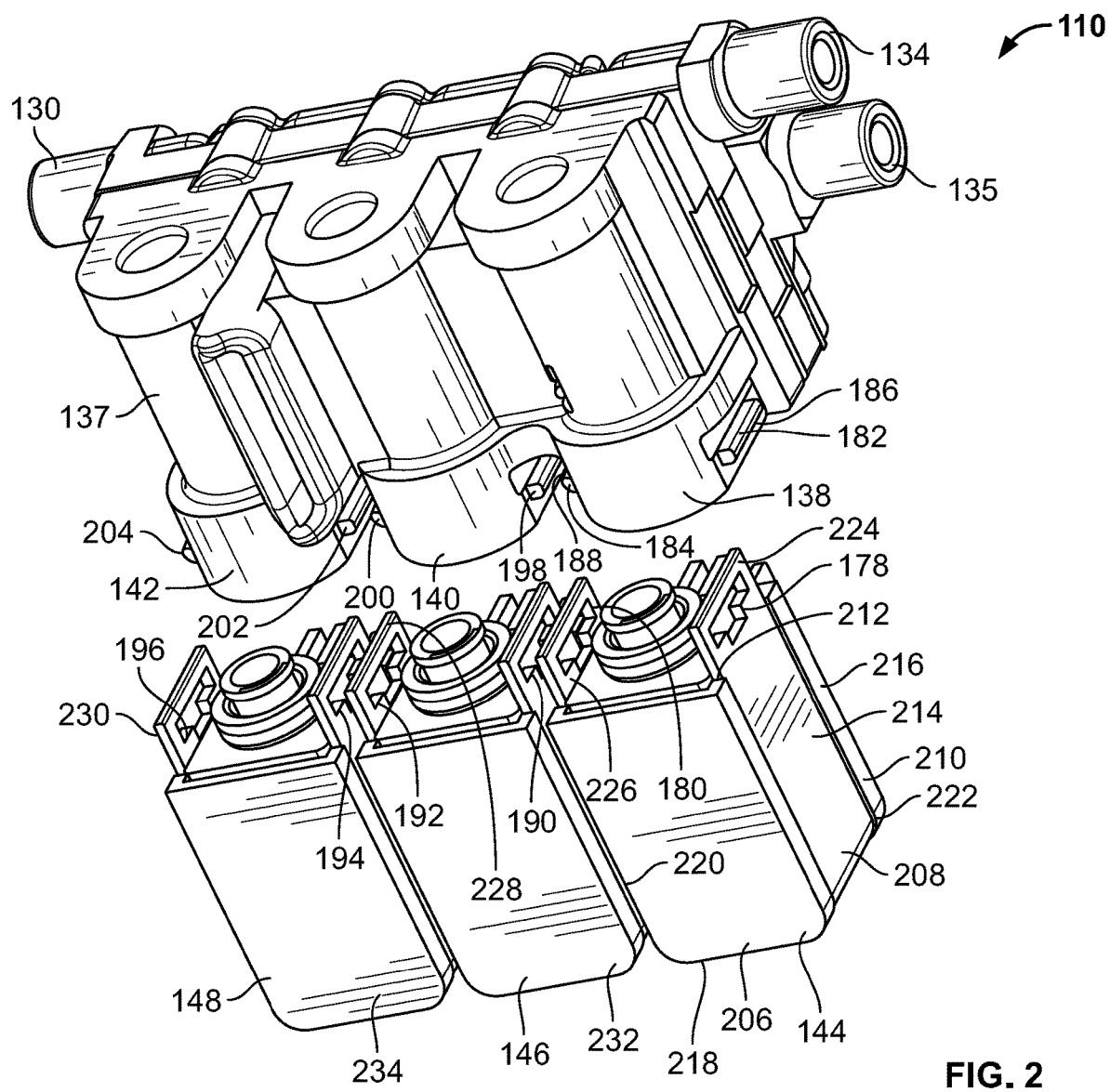
FIG. 2 illustrates an isometric partially expanded view of a specific example of the product manifold of the portable oxygen concentrator of FIG. 1.
Figure 3:
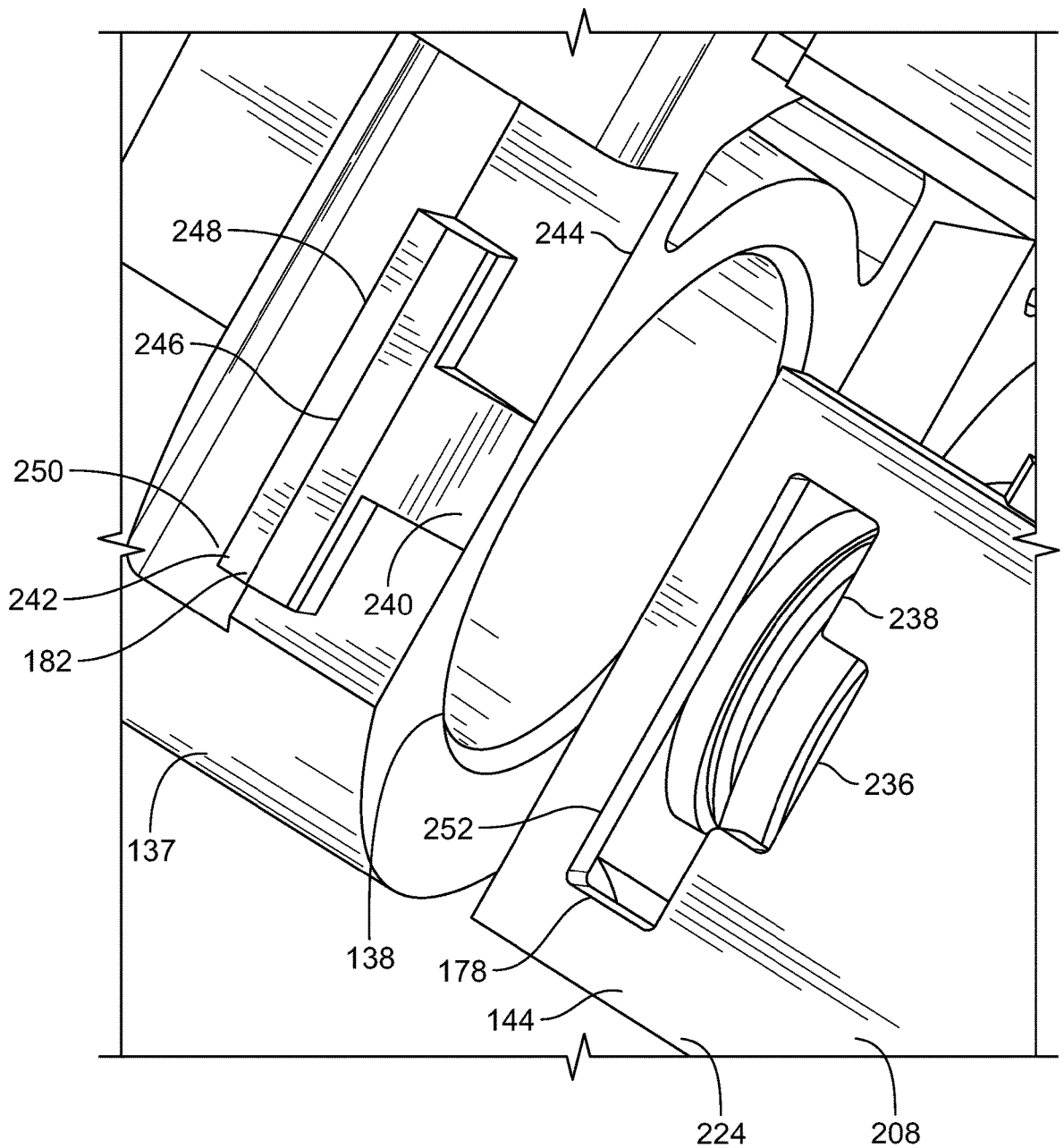
FIG. 3 illustrates a detailed partially expanded view of the product manifold of FIG. 2 showing a first control port, the body of the product manifold, and the first solenoid valve assembly.
Figure 4:
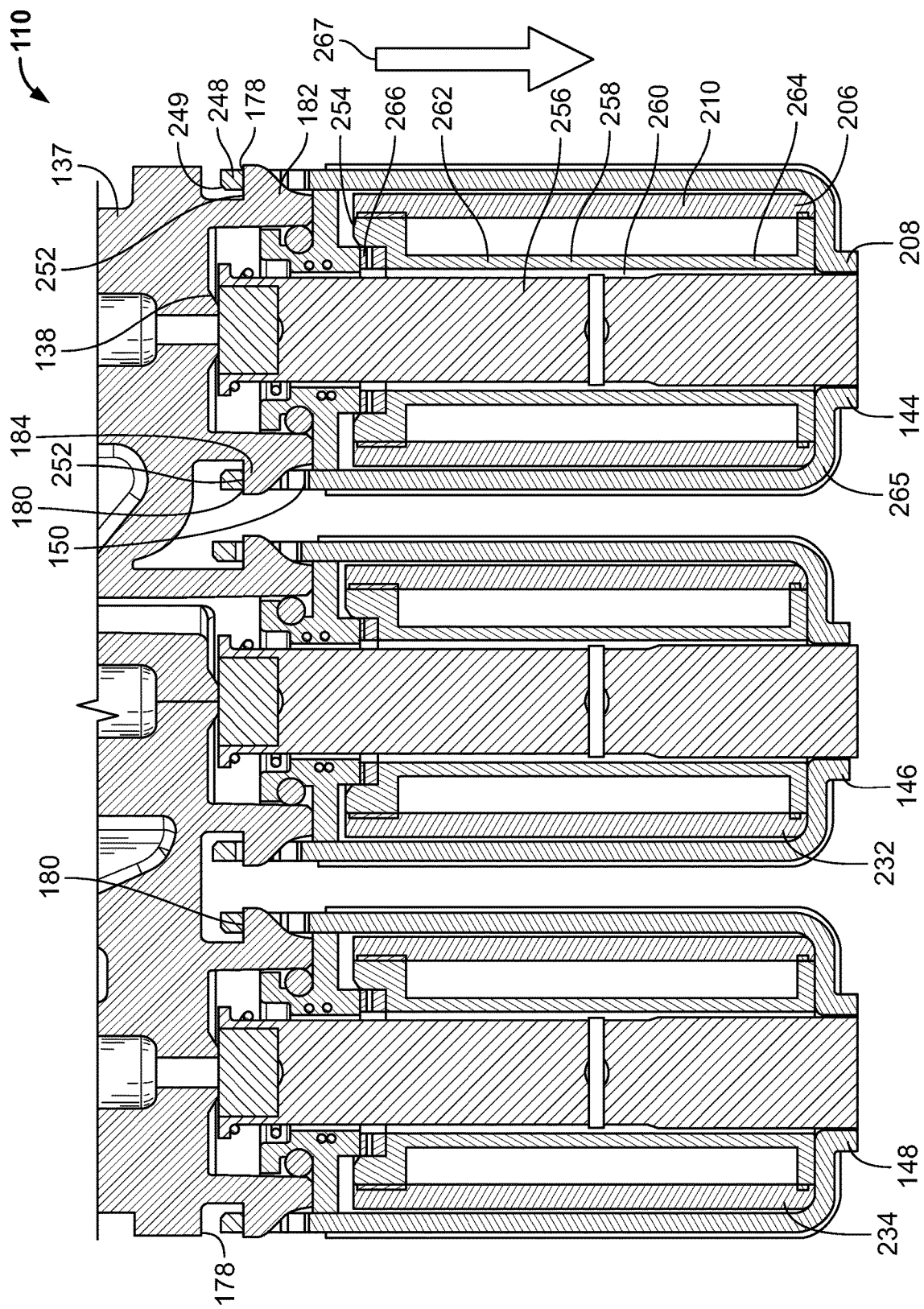
FIG. 4 illustrates a fragmentary cross-sectional view illustrating the first, second, and third solenoid valve assemblies and the snap fit connectors formed between the solenoid valve assemblies and the body of the product manifold.

FIG. 2 illustrates an isometric partially expanded view of a specific example of the product manifold 110 of the portable oxygen concentrator 100 of FIG. 1; FIG. 3 illustrates a detailed view of the first control port 138, the body 137 of the product manifold 110 and the first solenoid valve assembly 144; FIG. 4 illustrates a fragmentary cross-sectional view illustrating the first, second, and third solenoid valve assemblies 144, 146, 148 and the snap fit connectors 150, 152, 154 formed between the solenoid valve assemblies 144, 146, 148 and the body 137 of the product manifold 110; and FIG. 5 illustrates an enlarged fragmentary cross-sectional view of a portion of the first solenoid valve assembly 144, the first control port 138, and the snap fit connector 150.

Figure 5:
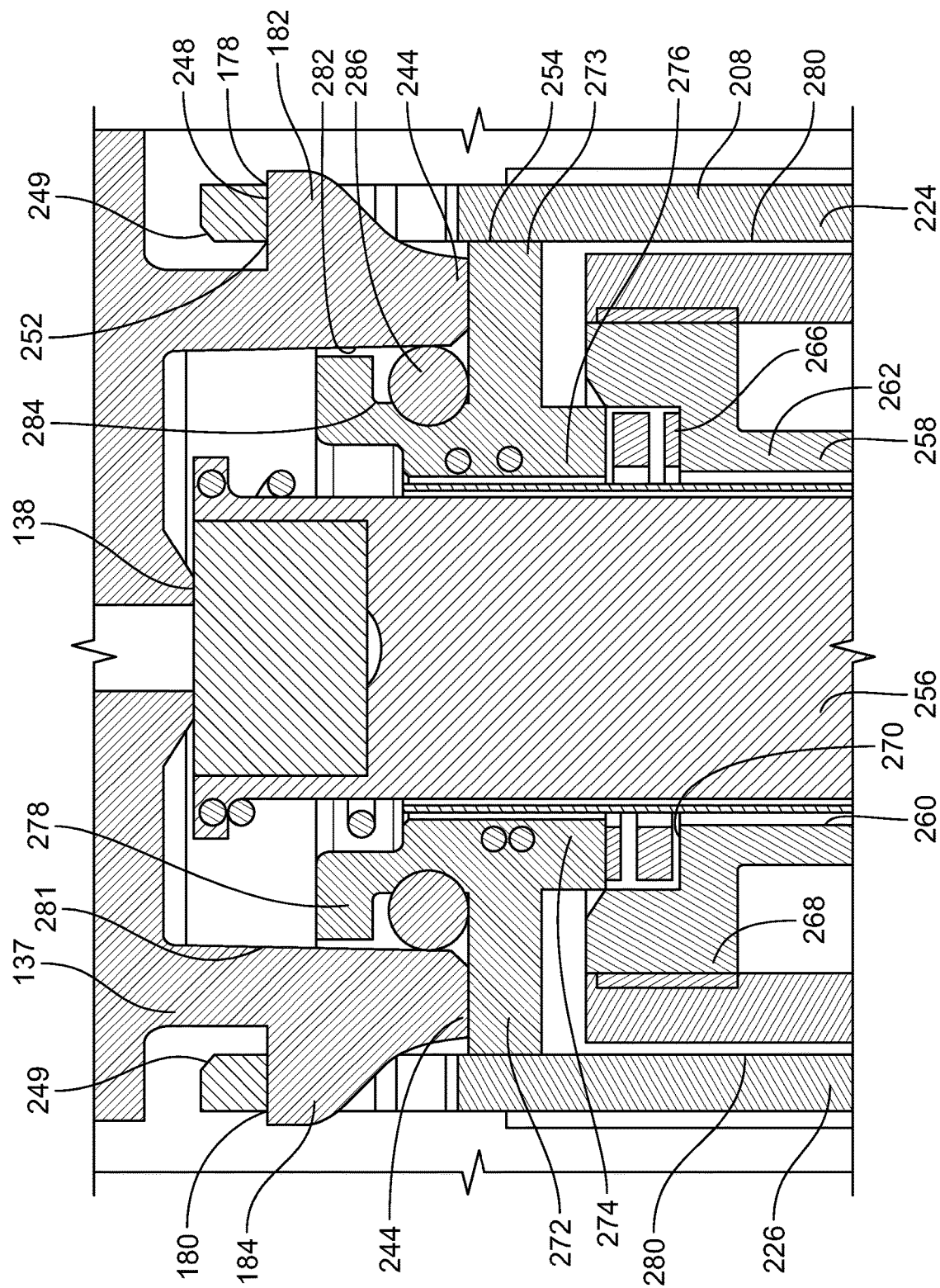
FIG. 5 illustrates an enlarged fragmentary cross-sectional view of a portion of the first solenoid valve assembly, the first control port, and the snap fit connector.

Referring to FIG. 2, with reference to FIGS. 3, 4 and 5, the first solenoid valve assembly 144 includes a first opening 178 and a second opening 180 and the body 137 of the product manifold 110 includes a first ramp 182 and a second ramp 184. In the example shown, the first ramp 182 is disposed on a first side 186 of the first control port 138 and the second ramp 184 is disposed on a second side 188 of the first control port 138. To form the snap fit connector 150 between the first solenoid valve assembly 144 and the body 137 of the product manifold 110, the first opening 178 is adapted to receive the first ramp 182 and the second opening 180 is adapted to receive the second ramp 184. The first and second openings 178, 180 are T-shaped and the first and second ramps 182, 184 are T-shaped. However, the openings 178, 180 and the ramps 182, 184 may have any corresponding shape. For example, the openings 178, 180 may have a rectangular shape and the ramps 182, 184 may have a corresponding rectangular shape.

The second and third solenoid valve assemblies 146, 148 also have openings 190, 192, 194, 196 and the body 137 of the product manifold 110 includes additional pairs of ramps 198 and 200, 202 and 204. The ramps 198, 200, 202, 204 are disposed adjacent the corresponding second control port 140 and the third control port 142. The openings 190, 192 of the second solenoid valve assembly 146 are adapted to receive the ramps 198, 200 adjacent the second control port 140 and the openings 194, 196 of the third solenoid valve assembly 148 are adapted to receive the ramps 202, 204 adjacent the third control port 142.

In the example shown, the first solenoid assembly 144 includes a first solenoid valve 206 and a first bracket 208. The first bracket 208 includes the openings 178, 180. The first solenoid valve 206 includes a housing 210. The housing 210 defines a groove 212. A portion 214 of the first bracket 208 is disposed within the groove 212.

In the example shown, the first bracket 208 is a U-shaped bracket and the first solenoid valve 206 includes a first side 216, a second side 218, and a third side 220. The portion 214 of the first bracket 208 is received within the groove 212 of the housing 210 and surrounds a portion 222 of the first, second, and third sides 216, 218, 220.

The first bracket 208 includes a first leg 224 and a second leg 226. The first leg 224 defines the first opening 178 and is shown engaging the first side 216 of the first solenoid valve 206 and the second leg 226 defines the second opening 180 and is shown engaging the second side 218 of the first solenoid valve 206. While the first solenoid valve assembly 144 is shown including the first bracket 208 to secure the first solenoid valve 206 to the body 137 of the product manifold 110, the first solenoid valve 206 may be coupled to the body 137 in different ways. For example, instead of including a U-shaped bracket, legs defining the openings 178, 180 may be coupled to and extend from the housing 210 of the first solenoid valve 206.

While the above description discloses details of the first solenoid valve assembly 144, the second and third solenoid valve assemblies 146, 148 may have similar or the same structure. For example, the second and third solenoid valve assemblies 146, 148 include brackets 228, 230 defining the openings 190, 192, 194, 196 that surround corresponding solenoid valves 232, 234.

Referring to FIG. 3, a detailed view of the first opening 178 and the first ramp 182 are illustrated. In the example shown, the first opening 178 includes a first opening portion 236 and a second opening portion 238 and the first ramp 182 includes a first ramp portion 240 and a second ramp portion 242. The first opening portion 236 is contiguous with the second opening portion 238 and forms a T-shaped opening. The first ramp portion 240 begins at or adjacent to an edge 244 of the body 137 of the product manifold 110 and tapers outwardly toward the second ramp portion 242. The first ramp portion 240 is contiguous with the second ramp portion 242. The second ramp portion 242 includes a rounded surface 246 and a rear surface 248. The rounded surface 248 and/or the first ramp portion 240 may be adapted to easily expand the first bracket 208 with less force being applied (e.g., reduces friction). The rear surface 248 and an adjacent surface 250 of the body 137 of the product manifold 110 form a locking step.

When the first bracket 208 is urged onto the body 137 of the product manifold 110 and over the first and second ramps 182, 184, the first ramp 182 is received by the first opening 178 after an edge 252 forming the second opening portion 238 passes the rear surface 248 of the first ramp 182. Thus, in an example, the first bracket 208 is elastically deformable to allow the legs 224, 226 of the first bracket 208 to extend outwardly prior to the openings 178, 180 receiving the ramps 182, 184 and forming the snap fit connection 150. In the example shown, an inward facing surface 249 of the first bracket 208 is rounded. The inward facing surface 249 is adapted to reduce an amount of friction encountered when the first bracket 208 is being urged onto the first and second ramps 182, 184. The first bracket 208 may be made of plastic, metal or any other suitable material. As an example, the first bracket 208 may be formed of 430F stainless steel with a 22-gage size. However, other materials and/or other thicknesses may be used instead.

Referring to FIG. 4 with reference to FIG. 5, the housing 210 of the first solenoid valve assembly 144 includes an opening 254. The opening 254 faces the first control port 138. A control element 256 is disposed within the housing 210. The control element 256 is shiftable between a first position and a second position relative to the first control port 138. In an example, in the first position, the control element 256 seats against the first control port 138 and prevents fluid flow out of the outlet port 135 (See, FIG. 1), and, in the second position, the control element 256 is spaced from the first control port 138 and allows fluid flow out of the outlet port 135 (See, FIG. 1).

A control element guide 258 is disposed within the housing 210 of the first solenoid valve assembly 144. The control element guide 258 has a bore 260. The control element 256 is received within the bore 260. An interaction between the control element guide 258 and the control element 256 at least partially guides the movement of the control element 256 relative to, for example, the first control port 138.

In the example shown, the control element guide 258 includes a first portion 262 and a second portion 264. The first portion 262 is disposed adjacent the opening 254. The second portion 264 of the control element guide 258 engages an end 265 of the first bracket 208. Thus, in this example, the first bracket 208 forms a bottom surface of the first solenoid valve assembly 144. Alternatively, in another example, the housing 210 of the first solenoid valve assembly 144 may include a bottom surface against which the second portion 264 of the control element guide 258 engages.

A biasing element 266 is disposed between the first portion 262 of the control element guide 258 and the body 137 of the product manifold 110. The biasing element 266 may be one or more wave springs. However, other springs such as a helical compression spring may be used instead. The biasing element 266 urges the first solenoid valve assembly 144 in a direction generally indicated by arrow 267 and, thus, biases the snap fit connector 150 between the first solenoid valve assembly 144 and the body 137 of the product manifold 110. Specifically, the biasing element 266 urges the edges 252 defining the first and second openings 178, 180 into engagement with the rear surface 248 of the first and second ramps 182, 184. In an example, the biasing element 266 is adapted to support the first bracket 208 and is adapted to accommodate for stack-up tolerances in the first solenoid valve assembly 144, the body of the manifold 110, etc.

Referring to FIG. 5, the first portion 262 of the control element guide 258 includes a flange 268 that forms a spring seat 270. The biasing element 266 is positioned within and engages the spring seat 270. A plug 272 is positioned between the first and second legs 224, 226 of the first bracket 208. The biasing element 266 is positioned between the plug 272 and the first portion 262 of the control element guide 258. The position of the biasing element 266 relative to the plug 272 allows for the biasing element 266 to urge the plug 272 against the edge 244 of the body 137.

The plug 272 includes a flange 273 and a collar 274 including a first collar portion 276 and a second collar portion 278. The flange 273 slidably engages inner surfaces 280 of the first bracket 208. The first collar portion 276 is adapted to be received within the spring seat 270 and/or to engage the biasing element 266. The second collar portion 278 extends into a portion 281 of the first control port 138 including an inner surface 282. In the example shown, the second collar portion 278 includes a seal groove 284. A seal 286 is disposed within the seal groove 284 and is adapted to sealingly engage the inner surface 282 of the first control port 138. The seal 286 may be an O-ring.

While the above description discloses structure of the first solenoid valve assembly 144, the first control port 138, and the first snap fit connector 150, the structure of the second and third solenoid valve assemblies 146, 148, the second and third control ports 140, 142 and the second and third snap fit connectors 152, 154 may be the same or similar.

Further, while several examples have been disclosed herein, any features from any examples may be combined with or replaced by other features from other examples. Moreover, while several examples have been disclosed herein, changes may be made to the disclosed examples within departing from the scope of the claims.

What is claimed is:

1. A product manifold for use with a portable oxygen concentrator, the product manifold comprising:
   a body;
   a first product port, a second product port, an accumulator port, and an output port;
   a flow path fluidly coupling the first product port, the second product port, the accumulator port, and the output port;

a first control port, a second control port, and a third control port fluidly coupling the flow path; and a first solenoid valve assembly, a second solenoid valve assembly, and a third solenoid valve assembly;

wherein, the first, second, and third solenoid valve assemblies are secured to the body of the product manifold adjacent the first, second, and third control ports, respectively, by a corresponding snap fit connector; and wherein each snap fit connector includes a first opening and a second opening disposed on opposite sides of a corresponding one of the solenoid valve assemblies, and further includes a first ramp and a second ramp disposed on opposite sides of a corresponding one of the control ports, the first opening sized to receive a portion of the first ramp and the second opening sized to receive a portion of the second ramp to secure the corresponding solenoid valve assembly to the body of the product manifold, and wherein the first ramp comprises a T-shaped ramp and the first opening comprises a T-shaped opening.

2. The product manifold of claim 1, wherein the first solenoid valve assembly comprises a first solenoid valve and a first bracket, the first bracket comprising the first opening and the second opening.

3. The product manifold of claim 2, wherein the first solenoid valve comprises a housing having a groove, a portion of the first bracket disposed within the groove.

4. The product manifold of claim 3, wherein the first bracket being a U-shaped bracket, the first solenoid valve has a first side, a second side, and a third side, the portion of the U-shaped bracket being received within the groove and surrounding a portion of the first side, the second side, and the third side of the first solenoid valve.

5. The product manifold of claim 4, wherein the U-shaped bracket comprises a first leg and a second leg, the first leg defining the first opening and engaging the first side of the first solenoid valve, the second leg defining the second opening and engaging the second side of the first solenoid valve.

6. The product manifold of claim 1, wherein the first solenoid valve assembly comprises a first housing having an opening facing the first control port, a control element being disposed within the first housing, the control element being shiftable between a first position and a second position relative to the first control port.

7. The product manifold of claim 6, further comprising a control element guide having a bore and being disposed in the first housing, the control element being at least partially disposed within the bore of the control element guide.

8. A product manifold for use with a portable oxygen concentrator, the product manifold comprising:

a body;

a first product port, a second product port, an accumulator port, and an output port;

a flow path fluidly coupling the first product port, the second product port, the accumulator port, and the output port;

a first control port, a second control port, and a third control port fluidly coupling the flow path; and a first solenoid valve assembly, a second solenoid valve assembly, and a third solenoid valve assembly;

wherein, the first, second, and third solenoid valve assemblies are secured to the body of the product manifold adjacent the first, second, and third control ports, respectively, by a corresponding snap fit connector;

wherein the first solenoid valve assembly comprises a first housing having an opening facing the first control port, a control element being disposed within the first housing, the control element being shiftable between a first position and a second position relative to the first control port; and further including a control element guide having a bore and being disposed in the first housing, the control element being at least partially disposed within the bore of the control element guide; and wherein the control element guide includes a first portion and a second portion, the first portion disposed adjacent the opening, further comprising a biasing element, the biasing element disposed between the first portion of the control element guide and the body of the product manifold to bias the corresponding snap fit connector between the first solenoid valve assembly and the body of the product manifold.

9. The product manifold of claim 8, wherein the first portion of the control element guide forms a spring seat, the biasing element engaging the spring seat.

10. The product manifold of claim 8, further comprising a plug, the biasing element disposed between the plug and the first portion of the control element guide.

11. The product manifold of claim 10, wherein the plug includes a collar and the first control port includes an inner surface, the collar includes a seal groove, further comprising a seal disposed within the seal groove, the seal being adapted to sealingly engage the inner surface of the first control port.

12. A portable oxygen concentrator, comprising:

a compressor;

a waste/feed manifold, comprising:
  an inlet port coupled to the compressor;
  a pair of three-way valves, each three-way valve having a first port, a second port, and a third port, the first port coupled to the compressor; and
  an exhaust port, the second port of each of the three-way valves fluidly coupled to the exhaust port;

a first sieve bed and a second sieve bed, each of the sieve beds coupled to the third port of one of the three-way valves;

a product manifold, comprising:
  a body;
  a first product port and a second product port, the first product port coupled to the first sieve bed, the second product port coupled to the second sieve bed;
  an accumulator port;
  an output port;
  a flow path fluidly coupling the first product port, the second product port, the accumulator port, and the output port;
  a first control port, a second control port, and a third control port fluidly coupling the flow path; and
  a first solenoid valve assembly, a second solenoid valve assembly, and a third solenoid valve assembly, wherein, the first, second, and third solenoid valve assemblies are secured to the body of the product manifold by a corresponding snap fit connector;

wherein each solenoid valve assembly is secured to the body of the product manifold adjacent to a corresponding one of the first, second, or third control ports by one of the corresponding snap fit connectors; and wherein each snap fit connector includes a first opening and a second opening disposed on opposite sides of a corresponding one of the solenoid valve assemblies, and further includes a first ramp and a second ramp disposed on opposite sides of a corresponding one of the control ports, the first opening sized to receive a portion of the first ramp and the second opening sized to receive a portion of the second ramp to secure the corresponding solenoid valve assembly to the body of the product manifold, and wherein the first ramp comprises a T-shaped ramp and the first opening comprises a T-shaped opening.

13. A product manifold for use with a portable oxygen concentrator, the product manifold comprising:
   a body;
   a first product port, a second product port, an accumulator port, and an output port;
   a flow path fluidly coupling the first product port, the second product port, the accumulator port, and the output port;
   a control port fluidly coupling the flow path; and
   a solenoid valve assembly being secured to the body of the product manifold by a snap fit connector, the snap fit connector comprising a first ramp, a second ramp, a first opening, and a second opening, the first opening being adapted to receive the first ramp and the second opening being adapted to receive the second ramp to form the snap fit connector between the solenoid valve assembly and the body of the product manifold, wherein the first ramp comprises a T-shaped ramp and the first opening comprises a T-shaped opening; and
   wherein the first ramp is disposed on a first side of the control port and the second ramp is disposed on a second side of the control port, the first opening being defined by the solenoid valve assembly and the second opening being defined by the solenoid valve assembly.

\* \* \* \* \*

UNITED STATES PATENT AND TRADEMARK OFFICE
CERTIFICATE OF CORRECTION

| | | |
|---|---|---|
| PATENT NO. | : 11,744,977 B2 | Page 1 of 1 |
| APPLICATION NO. | : 16/890649 | |
| DATED | : September 5, 2023 | |
| INVENTOR(S) | : James R. Ward et al. | |

It is certified that error appears in the above-identified patent and that said Letters Patent is hereby corrected as shown below:

In the Specification

At Column 1, Line 12, "manifolds" should be -- manifolds. --.

At Column 4, Line 38, "one the" should be -- one of the --.

At Column 5, Line 59, "back flow" should be -- backflow --.

At Column 7, Line 23, "reduces" should be -- reduced --.

Signed and Sealed this
Twenty-second Day of October, 2024

Katherine Kelly Vidal
*Director of the United States Patent and Trademark Office*